(12) United States Patent
Haindl

(10) Patent No.: US 11,141,571 B2
(45) Date of Patent: Oct. 12, 2021

(54) SAFETY PUNCTURING SYSTEM

(71) Applicant: Hans Haindl, Wennigsen (DE)

(72) Inventor: Hans Haindl, Wennigsen (DE)

( * ) Notice: Subject to any disclaimer, the term of this patent is extended or adjusted under 35 U.S.C. 154(b) by 182 days.

(21) Appl. No.: 15/555,809

(22) PCT Filed: Mar. 3, 2016

(86) PCT No.: PCT/EP2016/054576
§ 371 (c)(1),
(2) Date: Sep. 5, 2017

(87) PCT Pub. No.: WO2016/142274
PCT Pub. Date: Sep. 15, 2016

(65) Prior Publication Data
US 2018/0043139 A1 Feb. 15, 2018

(30) Foreign Application Priority Data
Mar. 6, 2015 (DE) ...................... 10 2015 003 026.4

(51) Int. Cl.
*A61M 25/09* (2006.01)
*A61M 25/06* (2006.01)

(52) U.S. Cl.
CPC .. *A61M 25/09041* (2013.01); *A61M 25/0618* (2013.01); *A61M 25/0643* (2013.01); *A61M 25/0905* (2013.01); *A61M 2025/09075* (2013.01)

(58) Field of Classification Search
CPC .......... A61M 25/0643; A61M 25/0631; A61M 25/09041; A61M 25/09; A61M 25/0905; A61M 2025/09133; A61M 2025/09091; A61M 2025/09125; A61M 2025/09075; A61M 2025/09083; A61M 2025/09175; A61M 2025/09116; A61M 2025/0183; A61M 2025/0186; A61B 2017/22049
See application file for complete search history.

(56) References Cited

U.S. PATENT DOCUMENTS

| | | | |
|---|---|---|---|
| 5,366,441 A | | 11/1994 | Crawford |
| 5,441,055 A | * | 8/1995 | Ales ................. A61M 25/0905 600/434 |
| 5,813,405 A | * | 9/1998 | Montano, Jr. ..... A61M 25/0905 600/585 |
| 6,022,369 A | * | 2/2000 | Jacobsen .......... A61B 17/12022 606/1 |

(Continued)

FOREIGN PATENT DOCUMENTS

DE 4434169 A1 3/1995
DE 102012104058 A1 11/2013

OTHER PUBLICATIONS

International Search Report And Written Opinion including English Translation of International Search Report from PCT/EP2016/054576 dated Jun. 15, 2016, 13 pages.

(Continued)

*Primary Examiner* — Amber R Stiles
*Assistant Examiner* — Alexandra Lalonde
(74) *Attorney, Agent, or Firm* — Westman, Champlin & Koehler, P.A.

(57) ABSTRACT

The present invention relates to a safety puncturing system comprising a cannula and a guidewire.

12 Claims, 13 Drawing Sheets

(56) References Cited

U.S. PATENT DOCUMENTS

| | | | |
|---|---|---|---|
| 6,193,706 B1* | 2/2001 | Thorud | A61M 25/0905 604/103.04 |
| 2002/0045843 A1 | 4/2002 | Barker et al. | |
| 2002/0133092 A1* | 9/2002 | Oslund | A61M 25/09 600/585 |
| 2003/0229317 A1 | 12/2003 | Ferguson et al. | |
| 2011/0276032 A1* | 11/2011 | Al-Rashdan | A61M 25/09 604/528 |
| 2012/0226341 A1* | 9/2012 | Schreck | A61F 2/966 623/1.12 |
| 2013/0274784 A1* | 10/2013 | Lenker | A61B 17/3417 606/185 |
| 2014/0088560 A1* | 3/2014 | Min | A61M 25/005 604/510 |
| 2014/0214005 A1* | 7/2014 | Belson | A61M 25/0606 604/510 |
| 2015/0105719 A1 | 4/2015 | Haindl | |
| 2016/0045716 A1* | 2/2016 | Golzar | A61M 25/09 604/510 |

OTHER PUBLICATIONS

Office Action from German Patent Application No. 10 2015 003 026.4, dated Oct. 26, 2015, 10 pages.

\* cited by examiner

SAFETY PUNCTURING SYSTEM

CROSS-REFERENCE TO RELATED APPLICATION

This Application is a Section 371 National Stage Application of International Application No, PCT/EP2016/054576, filed Mar. 3, 2016 and published as WO 2016/142274 A1, the contents of which are hereby incorporated by reference in their entirety.

The present invention relates to a puncturing system for safely introducing guidewires into blood vessels.

In accordance with regulatory rules in the U.S.A. and in Europe, exclusively puncturing systems which include safety provisions for preventing injuries caused by needle piercings should be used for risky punctures, which basically include punctures of blood vessels. However, these requirements are only applicable if such systems are indeed available for the respective purpose.

By now, safety systems of that kind have been available for numerous applications in medicine, but so far not for introducing guidewires and/or catheters in accordance with the so-called Seldinger technique. The Seldinger technique is a particularly gentle technique for introducing catheters into blood vessels. In accordance with this technique, the blood vessel is punctured by means of a relatively small cannula, and then a flexible guidewire is inserted into the blood vessel. The sharp cannula is then removed, and a catheter is inserted into the blood vessel either directly or by using a so-called lock. This catheter is guided by the guidewire that is already in the blood vessel. After the catheter has been inserted, the guidewire is withdrawn from the blood vessel.

Various safety devices which are attached to the nozzle of the cannula and can be folded laterally onto the cannula are already known and also in use for different cannulae (see, e.g., US 2003/0229317 A1). However, it is difficult to use them for Seldinger puncturing because in accordance with this technique often relatively deeply seated vessels are punctured and the cannula is moved in a wide variety of directions, and safety devices of this kind have turned out to be disturbing in this regard.

Therefore, it is the object of the present invention to provide a safety device for a puncturing system which is suitable for the Seldinger technique. This object is achieved by a safety puncturing system according to claim 1. Preferred embodiments of the invention are described, i.a., in the dependent claims.

The present invention accordingly relates to a safety puncturing system comprising a cannula and a guidewire. The cannula has a distal end with a bevel, a proximal end and a lumen for receiving the guidewire. The guidewire has a proximal section with a proximal end and a distal end as well as a distal section. The proximal section of the guidewire is releasably connected to the distal section of the guidewire. The proximal end of the proximal section of the guidewire preferably has an expanded region which is preferably dimensioned such that it cannot be introduced into the lumen of the cannula. Alternatively, the proximal end of the proximal section of the guidewire can have a locking or blocking section which prevents in an alternative manner that this section can be introduced into the lumen of the cannula. This can be realized, for example, by means of corresponding locking devices and/or sections having accordingly poor slide friction properties.

The invention is i.a. based on the fact that the guidewire, which is normally made as one piece, is made as two pieces, wherein a first proximal section is releasably connected to a second distal section. In accordance with the Seldinger technique, the distal section of the guidewire is introduced into a blood vessel by means of a cannula. The cannula is then removed from the blood vessel and withdrawn in the proximal direction. A part of the proximal section of the guidewire remains in the lumen of the cannula because the expanded region of the proximal end of the proximal section cannot be inserted into the lumen of the cannula. For now being able to use the distal section of the guidewire for introducing a catheter, the proximal section of the guidewire is disconnected from the distal section of the guidewire, wherein preferably the distal end of the proximal section of the guidewire projects distally beyond the distal end of the cannula so that the tip of the cannula or the bevel of the cannula is protected by this distal end.

In accordance with the present invention it is thus possible to leave the outer appearance of the cannula of a conventional Seldinger system completely unchanged so that the physician can make the puncture as usual. The system comprises a Seldinger puncturing cannula having any desired bevel, e.g. Cournand. The outer appearance of this cannula does not differ from that of a common Seldinger cannula and the handling thereof does not have to be changed. When the physician has then hit the blood vessel, he/she introduces a guidewire which does not differ from conventional guidewires in view of its distal end and can be packed in a dispenser as usual. The tip of the Seldinger wire can have any desired design, i.e. it can be a Seldinger wire having a straight tip, a J-tip or a slightly bent tip. Also particular configurations, for example, an extended soft section and the like are possible, just like in any other Seldinger wire. Only the proximal section of the guidewire, which by no means affects the functionality and flexibility of the system, has additional structural features. The proximal, releasable section can be imagined as a kind of metal or plastic extension, which, e.g., ends in a conical end piece over which the cannula cannot be drawn. The user thus draws the cannula back over the Seldinger wire until it slides onto this end piece. Then it can be released from the Seldinger wire together with the end piece, for example, by means of a connection having a specific design.

The expanded region or the locking or blocking section is preferably suitable for engaging with the proximal end of the cannula, preferably for locking therewith. The resulting connection is preferably not releasable, i.e. the expanded region and the proximal end preferably cannot be disconnected in a destruction-free manner Such a connection can be realized, e.g., in that the proximal end of the cannula has a syringe cone having an undercut and the expanded region has a corresponding projection or a corresponding protrusion which is suitable for locking with the undercut, preferably in a non-releasable manner.

It is preferred that the proximal section of the guidewire is dimensioned such that the distal end of the proximal section projects distally beyond the distal end of the cannula when the expanded region or the locking or blocking region of the guidewire adjoins the proximal end of the cannula or is engaged therewith. For this purpose, the cannula preferably has a first length and the proximal section of the guidewire has a second length being longer than the first length. This guarantees that the distal end of the proximal section of the guidewire projects distally beyond the distal end of the cannula having the bevel when the cannula has been removed from the blood vessel and the proximal section of the guidewire has again been disconnected from the distal section of the guidewire. At this time, i.e. after the tip of the cannula has come in contact with blood, the bevel of the cannula is then protected by the distal end of the proximal section of the guidewire so that unintended injuries can be avoided.

Basically, the proximal section and the distal section of the guidewire can be releasably connected with each other in a wide variety of manners. In accordance with a first preferred option, the proximal section and the distal section of the guidewire are connected by means of an area having a reduced material strength and/or a predetermined breaking point. For example, at the transition between the proximal and the distal section the diameter of the guidewire can be so much smaller than the diameter of the remaining guidewire that this connecting section can be easily broken by hand. The diameter of the guidewire in the connecting section is preferably smaller than 50%, more preferably smaller than 40%, particularly preferably smaller than 30% of the remaining diameter of the guidewire. The predetermined breaking point can alternatively also be achieved by means of a different material which is, for example, less tear-proof and/or break-proof than the material of the remaining guidewire. The predetermined breaking point can also be realized by a welded and/or soldered joint.

According to a further preferred alternative, the proximal section and the distal section of the guidewire can be releasably connected by means of two connecting elements or coupling elements. The distal end of the proximal section of the guidewire preferably has a first connecting element and a proximal end of the distal section has a second connecting element which can be releasably engaged with the first connecting element. For example, the first or second connecting element can have a thinned throat section and a rounded, expanded section and the respective other connecting element can have a corresponding receiving section having an expandable opening in which the rounded, expanded section can be inserted. The rounded, expanded section can be, e.g., spherical and the corresponding receiving section can be, e.g., hemispherical.

Alternatively, the first connecting element can have at least two spring elements having radially inwardly projecting projections and/or hooks, and the second connecting element can have one or more corresponding recess(es) and/or opening(s) with which the projections and/or hooks can engage. The at least two spring elements preferably spring radially outwardly, wherein the projections and/or hooks are preferably not engaged with the corresponding openings or recesses when the springs are unstressed. For example, the distal end of the proximal section of the guidewire can be made of a thin-walled tube. The distal end of this tube comprises at least two resilient, flat tongues having inwardly directed hooks at their distal ends. The corresponding recess at the proximal end of the distal section of the guidewire can, e.g., be formed by a wire helix in which the lead is larger than the wire diameter.

Moreover, it is preferred that a movable sleeve is arranged around the guidewire in the area of the connection of the proximal section of the guidewire to the distal section of the guidewire. This sleeve can be made, e.g., of plastic or metal and should prevent the connection formed by the connecting elements from being disconnected early. When withdrawing the cannula over the guidewire, this sleeve is preferably taken along and remains in the nozzle of the cannula. As soon as the connection or the connecting elements exit(s) the tip of the cannula, it/they can be disconnected without any problems.

Moreover, the distal end of the proximal section of the guidewire can be provided with a further protecting element, wherein this further protecting element can also be realized by, e.g., the first connecting element. This further protecting element serves for covering the bevel of the cannula at least partly and/or for protecting it in view of a potential risk of injury. This further protecting element can, for example, be a conical, preferably elastic collar or projection at the distal end of the proximal section of the guidewire. When the cannula is withdrawn so much that the distal end of the proximal section of the guidewire projects distally beyond the distal end of the cannula, this collar or projection can expand radially outwardly and accordingly project radially beyond the bevel of the cannula and thus cover it. Instead of a collar or a projection, it is also possible to provide a cone-shaped wire helix which relaxes when exiting the cannula tip and accordingly expands in the radial direction. The distal end of the proximal section of the guidewire can alternatively or additionally comprise a tubular section having a plurality of longitudinal cuts, wherein the struts of the tube are expanded in a bulging manner between the longitudinal cuts. Also the spring elements having the radially inwardly projecting projections and/or hooks as mentioned above can serve as a further protecting element, wherein these spring elements can at the same time also function as a connecting element.

It is preferred that the expanded region of the guidewire is suitable for engaging with the proximal end of the cannula, preferably in a non-releasable manner, preferably for locking therewith, wherein the protecting element covers the bevel of the cannula when the expanded region of the guidewire engages with the proximal end of the cannula.

According to a preferred embodiment of the present invention, at the proximal end of the distal section the guidewire or core wire is welded to a connecting element in the form of an outer shell of the Seldinger wire some millimeters, preferably 1-5 mm, in front of the proximal end. This outer shell projects beyond the core wire by some millimeters, preferably 1-5 mm, and does not have a sphere at its end, but the helix tapers in a hemispherical manner so that a hole, which corresponds to approx. half the inner diameter of the helix, is formed in the center. This hole houses a preferably spherical head of a straight extension piece of the Seldinger wire, which can be of metal or plastic and forms the proximal section of the guidewire. By tilting this extension piece laterally, it can be removed from the end of the Seldinger wire, so that after removal of this extension wire the handling properties of the Seldinger wire are practically the same as that of any other Seldinger wire.

Alternatively, the extension piece can be connected by welding and/or soldering but it can be easily broken off by bending it laterally.

The procedure is such that the cannula is used for puncturing and the Seldinger wire is introduced. Then, the cannula is withdrawn over the Seldinger wire until the straight extension end is inside the cannula and locks therein with a suitable mechanism in the nozzle of the cannula or in front of the tip of the cannula. The coupling point of the extension piece is now in front of the tip of the cannula, and the cannula can be disconnected from the Seldinger wire by laterally bending with the extension piece. In this state, the end of the extension projects from the tip of the cannula and thus protects the user from puncturing himself/herself with the bevel of the cannula. When the cannula is relief-ground, this already provides for complete protection because in this case the tip directly attaches to the extension of the Seldinger wire.

In case a normal facet cut is used, in which in this state the tip of the cannula projects slightly beyond the extension of the Seldinger wire, the risk of injury is also reduced. However, the protection from injury can be improved even further by designing this extension of the Seldinger wire, for example, in such a manner that it enlarges its diameter in front of the tip of the Seldinger cannula. For example, this can be achieved in that an extension piece that is preferably made of plastic has an umbrella-like collar which, when being drawn through the cannula, attaches to this extension and expands again as soon as it has exited the tip of the cannula and thus protects the cannula tip.

A further possibility is that the extension of the Seldinger wire has a small necking in front of the cannula tip, wherein a key ring-shaped wire helix is located on this necking. This wire helix would be compressed in the conical nozzle of the cannula and could pass the cannula. After exiting the cannula tip, it would expand again, then lie in front of the cannula tip and thus protect it. As soon as it has been disconnected from the Seldinger wire, the Seldinger cannula would thus be protected at its tip and could no longer injure the user or others. For the extension of the Seldinger wire not being able to slide back, it can either lock automatically in the cannula nozzle, or it is prevented from sliding back by the above-described mechanisms in front of the tip.

A further possibility is that the extension is formed of a tube which has longitudinal cuts in front of the cannula tip and the tube walls therebetween are resiliently bulged outwardly.

The present invention further relates to a method for puncturing a blood vessel in an injury-proof manner by using the safety puncturing system according to the present invention. To this end, a blood vessel is punctured by means of the cannula and then the distal section of the guidewire is introduced into the lumen of the cannula. The cannula is then removed from the blood vessel and withdrawn in the proximal direction until the distal end of the proximal section of the guidewire projects distally beyond the distal end of the cannula. The proximal section is then disconnected from the distal section, wherein the proximal section remains at least partly in the lumen of the cannula.

In the following, the invention will be described in more detail with reference to the Figures in which FIG. 1 shows a side view of a preferred embodiment of the puncturing system according to the invention;

FIGS. 1 to 4 show different views of a first preferred embodiment of the safety puncturing system according to the present invention.

Figure 2:
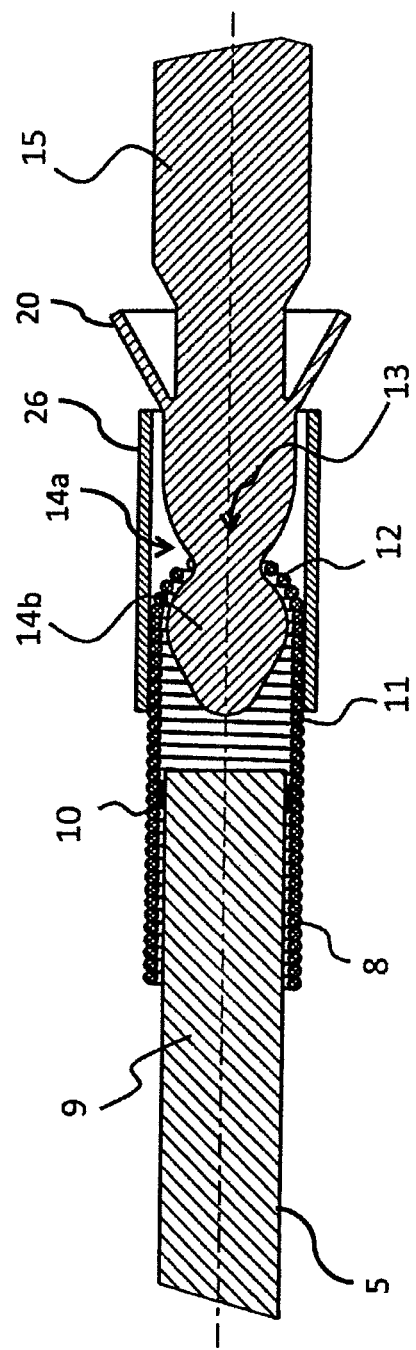
FIG. 2 shows a longitudinal sectional view of the connecting section between the proximal and the distal section of the guidewire according to a preferred embodiment.
Figure 8:
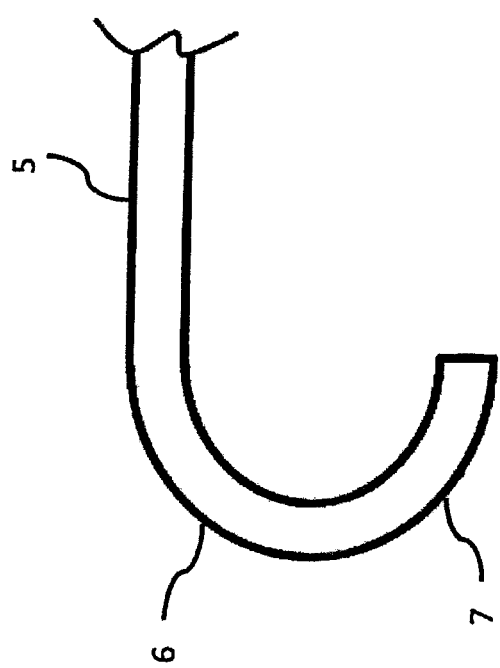
FIG. 8 shows a J-shaped distal tip of the guidewire.

The system comprises a cannula 1 and a guidewire 5 which basically comprises a proximal section 15 having a proximal end 16 and a distal end 16a as well as a distal section 6 being releasably connected with each other. The cannula 1 has a cannula tube 2 and a proximal end 3 having a projection with a female syringe cone, wherein the cannula tube 2 has a bevel 4 at its distal tip. This bevel can have different shapes for different punctures. The distal end of the distal section 6 of the guidewire 5 can also be straight or have a so-called J-tip 7 (see FIG. 8). In the shown embodiment, the guidewire 5 has a core wire 9 (see FIG. 2) which can have different diameters along its length for controlling the flexibility as well as a helix 8 made of stainless steel. The core wire 9 is welded to the helix 8 at the welded joint 10. At the proximal end 11, the helix 8 projects some millimeters, preferably 1-5 mm, beyond the proximal end of the core wire 9 and is hollow in this region. At the outermost end the diameter of the helix is reduced so that the end has the shape of a hemisphere 12 having an opening 13 in its center. This opening 13 is elastically expandable. This opening 13 houses the spherical tip 14b of the guidewire extension 15, which forms the proximal section 15 and is preferably slightly longer than the cannula 1. The hemisphere 12 with the opening 13 on the one hand and the spherical tip 14b on the other hand thus form two corresponding connecting elements which can releasably engage with each other.

Figure 4:
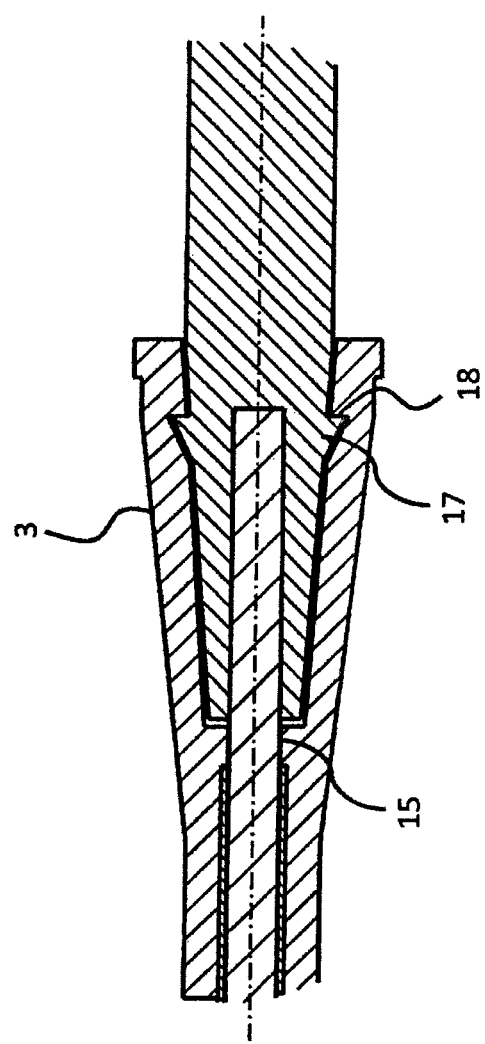
FIG. 4 shows a cross-sectional view of the connecting section between the proximal end of the guidewire and the proximal end of the cannula according to a preferred embodiment.

The proximal section 15 has preferably a diameter which corresponds to approximately the diameter of the distal section of the guidewire 5 and has, for example, a conical end piece 16 which fits into the syringe cone of the nozzle 3 of the cannula 1 at its proximal end. The cone of the end piece 16 can have locking hooks or projections 17 which can lock in a non-releasable manner with corresponding undercuts 18 in the syringe cone 3 (see FIG. 4).

Figure 1:
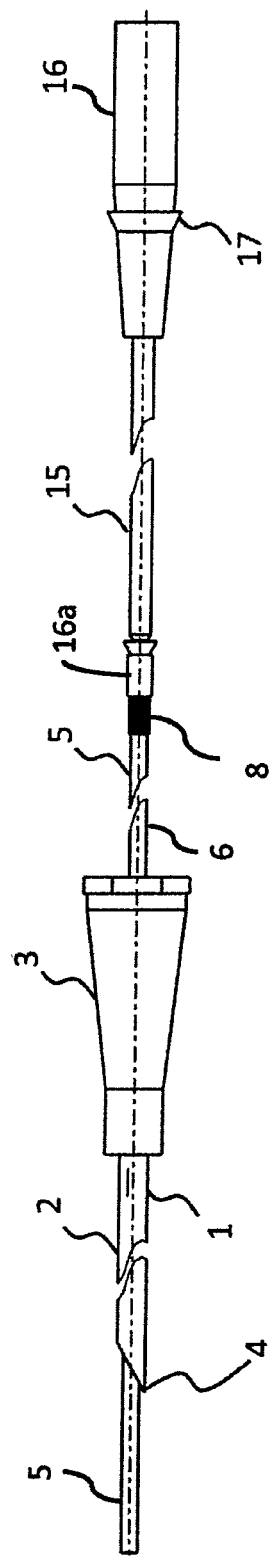

The guidewire 5 is inserted into the lumen of the cannula 1 in a state in which the proximal and the distal section are connected with each other, as shown in FIG. 1, after the cannula 1 has punctured a blood vessel. When it is intended to remove the cannula 1 after having inserted the guidewire 5, it cannot be drawn over this conical end piece 16. Rather, the entire proximal section 15 of the guidewire 5, on which the cannula 1 is now located, must be decoupled or disconnected from the distal section 6 of the guidewire. This is done by means of the connection or coupling comprising the hemispherical end 12 of the distal section 6 having the hole 13 on the one hand and the sphere 14b of the proximal section 15 on the other hand. By a lateral bending movement, the sphere 14b is disengaged from the opening 13 so that the proximal and the distal section are disconnected and the cannula 1 can be removed.

Figure 3:
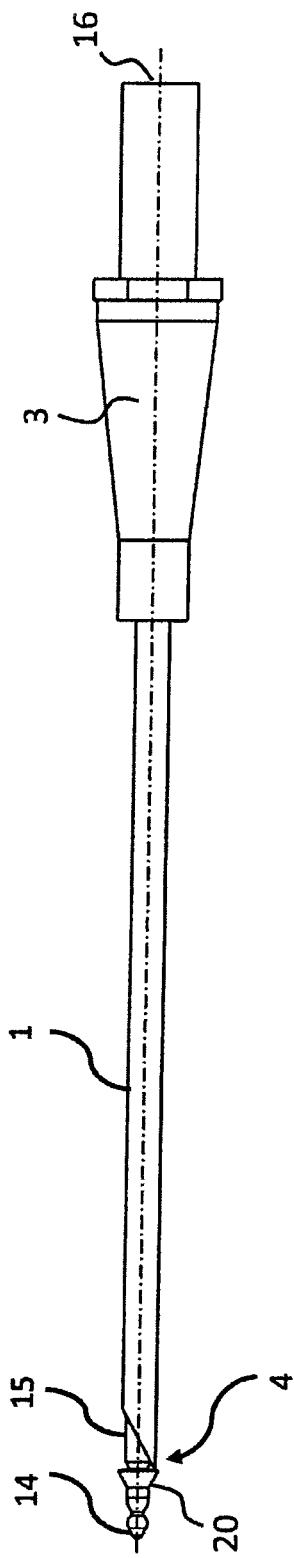
FIG. 3 shows a side view of the protected cannula according to a preferred embodiment.

Preferably, the proximal section or the extension 15 of the guidewire 5 is locked inside the cannula 1 with the aid of suitable means so that the extension 15 of the guidewire 5 projects beyond the tip of the cannula and thus the risk of injury caused by the cannula tip 4 is reduced (see FIG. 3). This locking can be realized, e.g., in the nozzle 3 of the cannula 1 by forming an undercut 18 therein, into which a resilient web 17 of the conical end piece 16 of the guidewire extension 15 locks (see FIG. 4).

Figure 5:
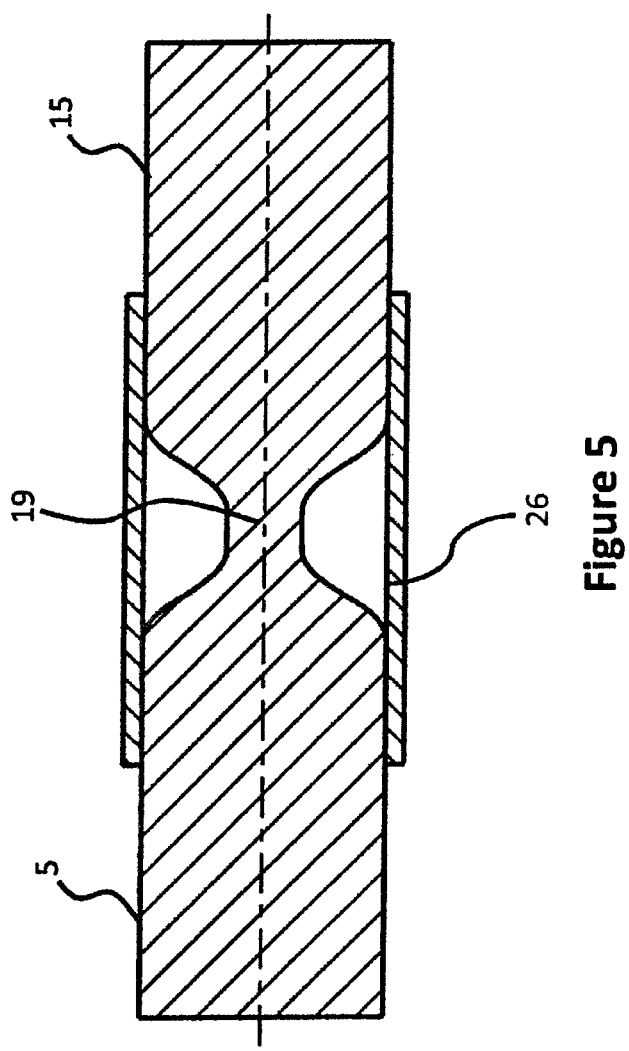
FIG. 5 shows a cross-sectional view of the connecting section between the proximal and the distal section of the guidewire according to a preferred embodiment.

Alternatively, the proximal and the distal section of the guidewire 5 can be connected with each other by means of a welded and/or soldered joint 19 (see FIG. 5) which can be broken off the guidewire by bending the extension. In this case (just like in the embodiment of FIGS. 1 to 4) a small sleeve 26 made of plastic or metal can be provided to avoid that the extension 15 of the guidewire 5 can be disconnected before the cannula has been withdrawn into the protected position. This sleeve is preferably arranged slidably on the connection or around the connecting section between the proximal and the distal section. The sleeve is preferably so stiff or rigid that bending or breaking of the welded joint 19 or the connection according to FIGS. 1 to 4 can be prevented effectively. When withdrawing the cannula 1 over the guidewire 5, this sleeve 26 is preferably taken along and remains in the nozzle of the cannula 1. As soon as the connection then exits the tip of the cannula, it can be disconnected without any problems.

A conical, elastic or flexible collar 20 which attaches to the outer circumference of the proximal section 15 when the cannula 1 is drawn over it, preferably at a region thereof having a reduced diameter, and which expands again after having left the tip 4 of the cannula 1 (see FIG. 3) is injection-molded to the proximal section 15 of the guidewire. Thus, this collar 20 prevents the cannula 1 from being disconnected from the proximal section, so that also the locking of the resilient web 17 with the undercut 18 as described above is not necessary. Moreover, this collar additionally protects the sharp cannula tip 4 or covers it so that injury becomes even less probable.

Figure 6:
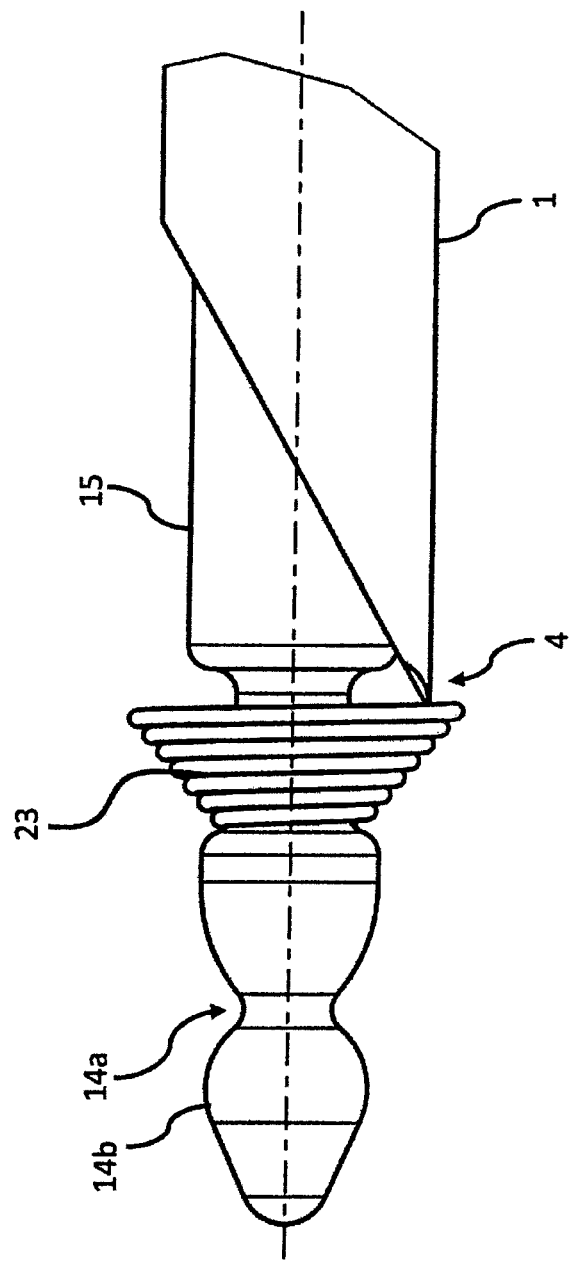
FIGS. 6 and 7 show protected cannula tips according to preferred embodiments.

Instead of this shield 20, also a small, conical wire helix 23 can be located on the proximal section 15 of the guidewire 5 (see FIG. 6), which can also attach to the guidewire when the cannula 1 is slipped over it and then expands again in front of the tip of the cannula and prevents removal of the guidewire extension 15 and also covers the tip 4 in such a manner that an injury becomes improbable.

Figure 7:
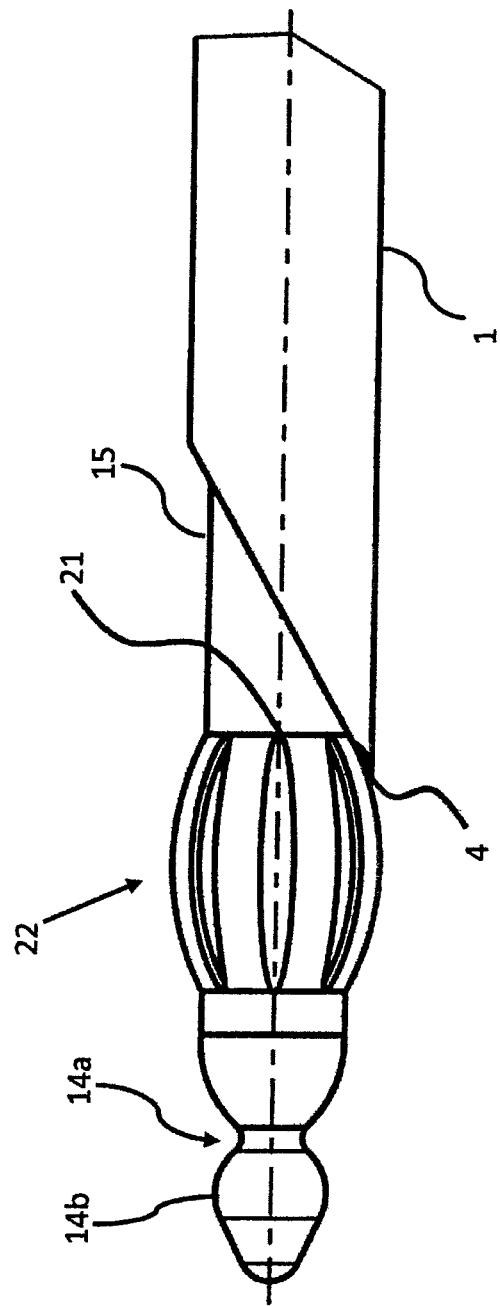

A further preferred embodiment of this additional cannula protection is realized in that the extension 15 is formed by a tube which, shortly after being coupled to the Seldinger wire, has a plurality of longitudinal slits 21 which are distributed across the circumference and bulged outwardly to form a circumferential bulge 22 but can be elastically bent back into the plane of the cannula axis so that they do not prevent the cannula 1 from being slipped over, but then expand in front of the cannula tip 2 in order to protect it from being touched (see FIG. 7).

Figure 9:
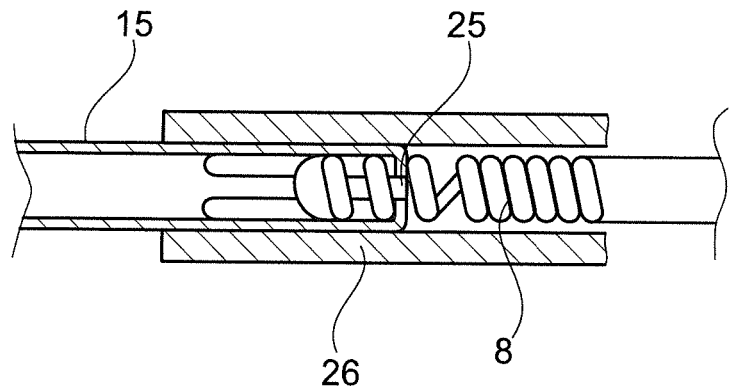
FIG. 9 shows a cross-sectional view of the connecting section between the proximal and the distal section of the guidewire according to a preferred embodiment.
Figure 10:
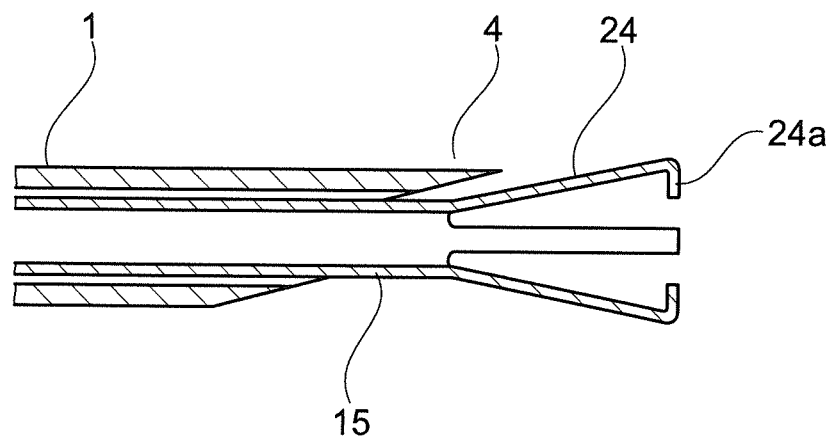
FIG. 10 shows a protected cannula and the use of the protecting element according to FIG. 9.

A further preferred embodiment of this additional cannula protection, which is shown in FIGS. 9 and 10, is realized in that a first connecting element which is provided at the proximal section 15 of the guidewire 5 comprises at least two spring elements 24 having radially inwardly projecting projections or hooks 24a. These projections of hooks 24a preferably engage with one or more recess(es) and/or opening(s) 25 which are part of a second connecting element 8 provided at the proximal end of the distal section (see FIG. 9). The at least two spring elements 24 preferably spring radially outwardly, wherein the projections and/or hooks 24a are preferably not engaged with the corresponding openings or recesses 25 when the springs are unstressed. In the shown preferred embodiment, the recesses are formed by free spaces 25 between neighboring, but spaced-apart windings of a wire helix 8. A sleeve 26 prevents radial movement of the spring elements 24 outwardly so that the proximal and distal sections of the guidewire remain releasably connected with each other. When the sleeve 26 is taken along when the cannula 1 is withdrawn, the hooks 24a can move freely outwardly and release the helices 8. In the expanded state shown in FIG. 10, the spring elements 24 then prevent the spring elements 24 from being drawn into the lumen of the cannula 1 so that the bevel 4 of the cannula is protected by the spring elements 24. In other words, also in this embodiment the additional protecting element (see FIG. 10) is formed by the first connecting element (see FIG. 9).

Figure 11:
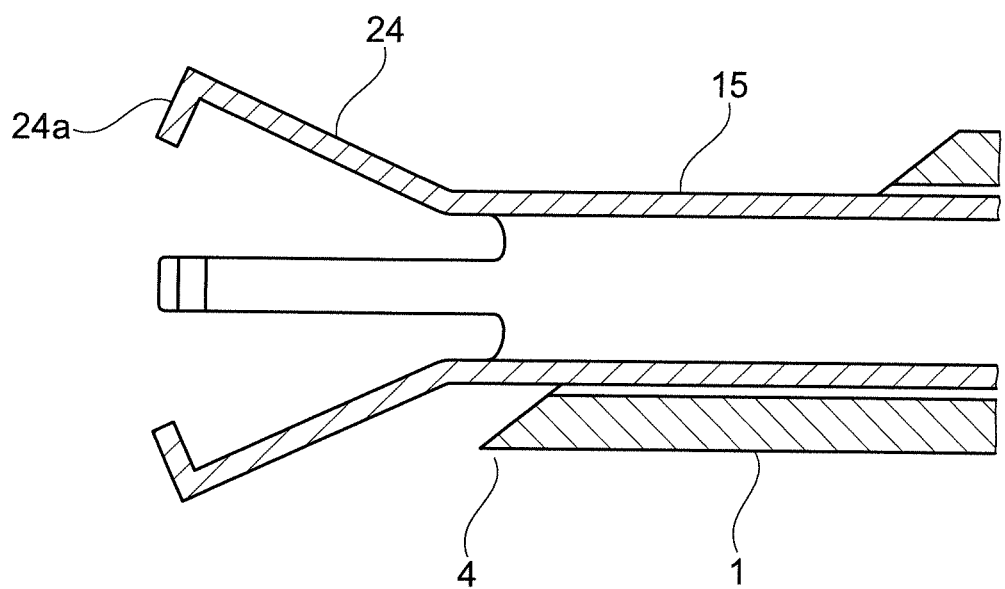
FIG. 11 shows a cross-sectional view of the connecting section between the proximal and the distal section of the guidewire according to a preferred embodiment.
Figure 12:
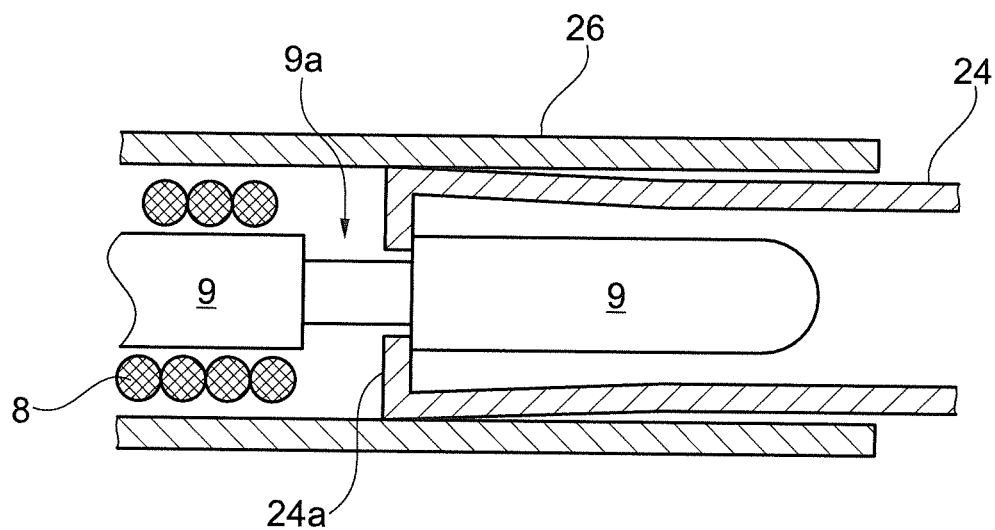
FIG. 12 shows a protected cannula and the use of the protecting element according to FIG. 11.

A similar embodiment is shown in FIGS. 11 and 12. Also in this embodiment the connecting element provided at the proximal section 15 of the guidewire 5 comprises at least two spring elements 24 having radially inwardly projecting projections or hooks 24a. As shown in FIG. 12, however, these projections or hooks 24a cannot only engage with recesses formed by free spaces 25 between neighboring, but spaced-apart windings of a wire helix 8. Rather, in this embodiment the projections or hooks 24a interact with a recess or groove 9a provided for this purpose in the core wire 9 which projects proximally beyond the helix 8.

Figure 13:
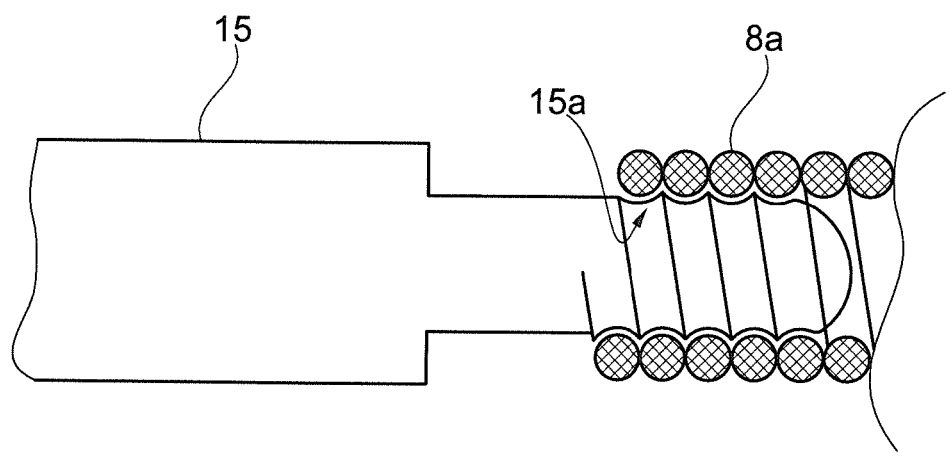
FIG. 13 shows a cross-sectional view of the connecting section between the proximal and the distal section of the guidewire according to a preferred embodiment.
Figure 14:
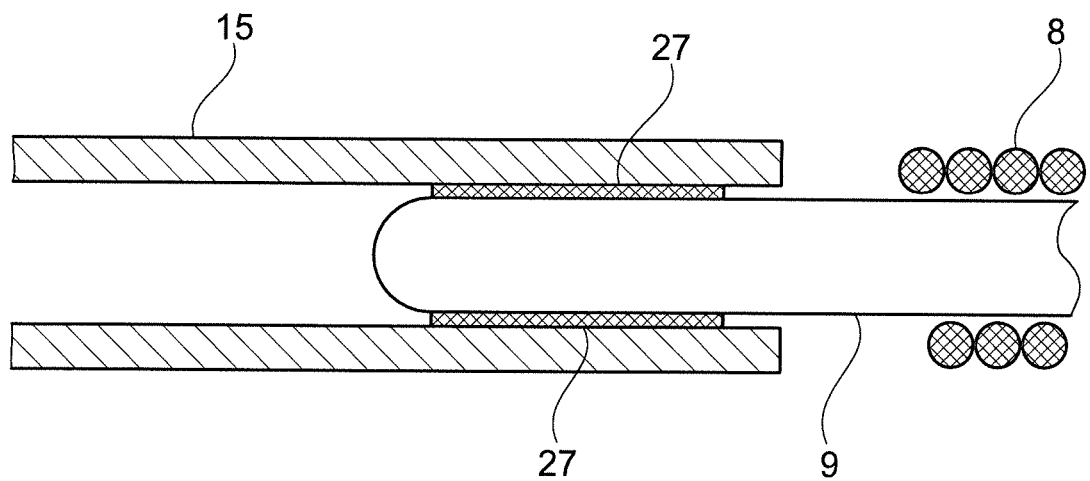
FIG. 14 shows a cross-sectional view of the connecting section between the proximal and the distal section of the guidewire according to a preferred embodiment.

FIGS. 13 and 14 schematically show two further possible ways for releasably connecting the proximal section 15 of the guidewire 5 to the core wire 9 of the guidewire 5. For example, the proximal section 15 can have an external thread 15a onto which the wire helix 8 (or another internal thread) can be screwed (see FIG. 13). Alternatively, the connection can also be realized by a releasable adhesive connection, for example a silicone layer 27 (see FIG. 14).

The invention claimed is:

1. A safety puncturing system, adapted to perform a Seldinger technique, for preventing needle stick injury to a user comprising a cannula and a flexible guidewire, wherein the cannula has a distal end having a bevel, a proximal end and a lumen for receiving the guidewire, wherein the guidewire has a proximal section having a proximal end and a distal end and a distal section, wherein the proximal section is releasably connected to the distal section and wherein the proximal end of the proximal section has an expanded region;

wherein the proximal end of the cannula has a syringe cone and an undercut and wherein the expanded region has a projection or a collar which is adapted to permanently lock with the undercut at the proximal end of the cannula; and wherein the distal end of the proximal section of the guidewire extends distally beyond the distal end of the cannula when the proximal end of the cannula and the expanded region of the guidewire are permanently locked, and wherein the bevel of the cannula is automatically protected by expansion of the projection or collar at the distal end of the proximal section of the guidewire to prevent needle stick injury of a user on removal of the cannula and proximal section of the guidewire to a point that the distal end of the proximal section of the guidewire projects distally beyond the distal end of the cannula.

2. The safety puncturing system according to claim 1, wherein the expanded region is dimensioned such that it cannot be introduced into the lumen of the cannula.

3. The safety puncturing system according to claim 1, wherein the cannula has a first length and the proximal section of the guidewire has a second length being longer than the first length.

4. The safety puncturing system according to claim 1, further comprising a movable sleeve which is arranged around the guidewire in an area of the connection of the proximal section of the guidewire to the distal section of the guidewire.

5. The safety puncturing system according to claim 1, further comprising a protecting element at the distal end of the proximal section of the guidewire.

6. The safety puncturing system according to claim 5, wherein the protecting element comprises one or a combination of the following elements: conical collar or projection; wire helix; tubular section having a plurality of longitudinal cuts forming tube struts, wherein the tube struts are expanded in a bulging manner between the longitudinal cuts; spring elements having radially inwardly projecting projections and/or hooks.

7. The safety puncturing system according to claim 5, wherein the expanded region of the guidewire is adapted to engage with the proximal end of the cannula, and wherein the protecting element is configured to project distally beyond the distal end of the cannula so that the bevel of the cannula is protected when the expanded region of the guidewire engages with the proximal end of the cannula.

8. The safety puncturing system according to claim 1, wherein the proximal section of the guidewire is releasably connected to the distal section of the guidewire by means of two connecting elements.

9. The safety puncturing system according to claim 8, wherein the distal end of the proximal section of the guidewire has a first connecting element and a proximal end of the distal section has a second connecting element which can releasably engage with the first connecting element.

10. The safety puncturing system according to claim 9, wherein the second connecting element has one or more recess(es) and/or opening(s) with which projections and/or hooks can engage.

11. The safety puncturing system according to claim 9, wherein the first connecting element has a thinned throat section and a rounded expanded section and/or wherein the second connecting element has a receiving section having an expandable opening.

12. The safety puncturing system according to claim 11, wherein the first connecting element has a spherical expanded section and/or wherein the second connecting element has a hemispherical receiving section.

* * * * *